United States Patent
Pieters et al.

(10) Patent No.: US 8,993,244 B2
(45) Date of Patent: Mar. 31, 2015

(54) SCREENING FOR COMPOUNDS HAVING IMMUNOSUPPRESSANT ACTIVITY BY TESTING IMPACT ON LEUKOCYTE-SPECIFIC CALCIUM FLUXES

(75) Inventors: Jean Pieters, Riehen (CH); Rajesh Jayac Han Dran, Basel (CH); Philipp Mueller, Inzlingen (DE)

(73) Assignee: University of Basel, Basel (CH)

( * ) Notice: Subject to any disclaimer, the term of this patent is extended or adjusted under 35 U.S.C. 154(b) by 1037 days.

(21) Appl. No.: 12/922,226

(22) PCT Filed: Mar. 12, 2009

(86) PCT No.: PCT/EP2009/052900
§ 371 (c)(1),
(2), (4) Date: Dec. 5, 2010

(87) PCT Pub. No.: WO2009/112542
PCT Pub. Date: Sep. 17, 2009

(65) Prior Publication Data
US 2011/0123994 A1 May 26, 2011

(30) Foreign Application Priority Data
Mar. 14, 2008 (EP) ..................... 08102603

(51) Int. Cl.
*G01N 33/53* (2006.01)
*G01N 33/50* (2006.01)
*G01N 33/68* (2006.01)

(52) U.S. Cl.
CPC ........ *G01N 33/5038* (2013.01); *G01N 33/6872* (2013.01); *G01N 2333/4712* (2013.01); *G01N 2500/10* (2013.01)
USPC ............................ 435/7.1; 435/7.21; 435/7.24

(58) Field of Classification Search
CPC ............. C08L 89/00; C08L 1/02; C08L 3/02; C08L 5/00; C08L 5/08; C08L 5/10; C08L 65/00; G01N 2800/52; G01N 33/57407; G01N 33/57415; G01N 33/57434; G01N 2500/00; G01N 33/574; G01N 33/57419; G01N 33/57423; G01N 33/6893; G01N 33/505; G01N 2500/10; G01N 33/5023; G01N 33/5047; G01N 33/56966; G01N 33/6803; C12N 5/0636; C12N 2320/10; A61K 2039/57; A61K 35/17; A01K 2217/075; A01K 2227/105; A01K 67/0276

USPC ......................... 435/7.1, 7.21, 7.24
See application file for complete search history.

(56) References Cited

U.S. PATENT DOCUMENTS

2005/0059618 A1  3/2005  Eulenberg et al.

FOREIGN PATENT DOCUMENTS

WO     2007/110385 A2    10/2007
WO    WO 2007110385 A2 * 10/2007

OTHER PUBLICATIONS

Mueller et al. Regulation of T cell survival through coronin-1-mediated generation of inositol-1,4,5-triphosphate and calcium mobilzation after T cell receptor triggering. Nature Immunology. Published online Mar. 16, 2008; 9 (4):424-431.*
Haraldsson M K et al: "The Lupus-Related Lmb3 Locus Contains a Disease-Suppressing Coronin-1A Gene Mutation" in Immunity, vol. 28, No. 1, Jan. 18, 2008, pp. 40-51.
Trimble William S et al: "TB or not TB: calcium regulation in mycobacterial survival." in CELL, vol. 130, No. 1, Jul. 13, 2007, pp. 12-14.
Nal B et al: "Coronin-1 expression in Tlymphocytes: Insights into protein function during T cell development and activation" in International Immunology, Oxford University Press, GB, vol. 16, No. 2, Feb. 1, 2004 pp. 231-240.
Mueller Philipp et al: "Regulation of T cell survival through coronin-1-mediated generation of inositol-1,4,5-trisphosphate and calcium mobilization after T cell receptor triggering" in Nature Immunology, vol. 9, No. 4, Apr. 2008, pp. 424-431.

* cited by examiner

*Primary Examiner* — Prema Mertz
(74) *Attorney, Agent, or Firm* — Joyce von Natzmer; Agris & von Natzmer LLP

(57) ABSTRACT

The invention relates to an assay for the identification of a compound having immunosuppressant activity, wherein a candidate compound is analyzed whether it blocks the $Ca^{2+}$ flux in coronin 1 expressing cells and/or in coronin 1 negative cells. A candidate compound is identified as having immunosuppressant activity if it blocks the $Ca^{2+}$ flux specifically in coronin 1 expressing cells. Further described are upstream assays wherein the impact of a candidate compound on coronin 1 trimerization is measured, and downstream assays wherein the impact of a candidate compound on diacyl glycerol (DAG) generation, phosphatidylinositol-4,5-biphosphate ($PIP_2$) levels and/or inositol-1,4,5-triphosphate ($InsP_3$) generation or on nuclear factor of activated T cells (NFAT) nuclear localization is determined.

4 Claims, 2 Drawing Sheets

```
                        SEQUENCE LISTING

<160> NUMBER OF SEQ ID NOS: 5

<210> SEQ ID NO 1
<211> LENGTH: 64
<212> TYPE: DNA
<213> ORGANISM: Artificial Sequence
<220> FEATURE:
<223> OTHER INFORMATION: synthetic construct, siRNA against mouse
      coronin1 forward

<400> SEQUENCE: 1
gatccccgac tggacgagta gacaagttca agagacttgt ctactcgtcc agtcttttttg    60 gaaa                                                                  64

<210> SEQ ID NO 2
<211> LENGTH: 64
<212> TYPE: DNA
<213> ORGANISM: Artificial Sequence
<220> FEATURE:
<223> OTHER INFORMATION: synthetic construct, siRNA against mouse
      coronin1 reverse

<400> SEQUENCE: 2
agcttttcca aaaagactgg acgagtagac aagtctcttg aacttgtcta ctcgtccagt    60
cggg                                                                  64

<210> SEQ ID NO 3
<211> LENGTH: 64
<212> TYPE: DNA
<213> ORGANISM: Artificial Sequence
<220> FEATURE:
<223> OTHER INFORMATION: synthetic construct, siRNA against human
      coronin1 forward

<400> SEQUENCE: 3
gatccccgcg cgtgcgcatc atcgagttca agagactcga tgatgcgcac gcgcttttg    60 gaaa                                                                  64

<210> SEQ ID NO 4
<211> LENGTH: 64
<212> TYPE: DNA
<213> ORGANISM: Artificial Sequence
<220> FEATURE:
<223> OTHER INFORMATION: synthetic construct, siRNA against human
      coronin1 reverse

<400> SEQUENCE: 4
agcttttcca aaaagcgcgt gcgcatcatc gagtctcttg aactcgatga tgcgcacgcg    60
cggg                                                                  64

<210> SEQ ID NO 5
<211> LENGTH: 32
<212> TYPE: PRT
<213> ORGANISM: Artificial Sequence
<220> FEATURE:
<223> OTHER INFORMATION: synthetic construct, peptide spanning
      trimerization domain of coronin 1
```

```
<400> SEQUENCE: 5

Val Ser Arg Leu Glu Glu Asp Val Arg Asn Leu Asn Ala Ile Val Gln
1               5                   10                  15

Lys Leu Gln Glu Arg Leu Asp Arg Leu Glu Glu Thr Val Gln Ala Lys
            20                  25                  30
```

SCREENING FOR COMPOUNDS HAVING IMMUNOSUPPRESSANT ACTIVITY BY TESTING IMPACT ON LEUKOCYTE-SPECIFIC CALCIUM FLUXES

This is the U.S. national stage of International application PCT/EP2009/052900, filed Mar. 12, 2009 designating the United States and claiming priority from European patent application EP 08102603.1, filed Mar. 14, 2008, both of which are incorporated herein by reference in their entirety.

FIELD OF THE INVENTION

The invention relates to a method for screening for suitable candidate compounds having immunosuppressant activity by measuring their impact on coronin 1 dependent $Ca^{2+}$ flux using coronin 1 protein expressing cells and comparing with coronin 1 negative cells.

BACKGROUND OF THE INVENTION

T cells normally get activated upon stimulation of their T cell receptors (TCR) present on their cell surface. Physiologically this happens when a T cell encounters an antigen presenting cell, like dendritic cells or B cells, displaying major histocompatibility complex (MHC) molecules loaded with antigenic peptide fragments. This in turn results in recruitment and activation of multiple cytosolic proteins such as phospholipase C (PLC), linker for activation of T cells (LAT) and src homology (SH)2 domain-containing leukocyte-specific phosphoprotein of 76 kDa (SLP-76). Activation of PLC leads to the generation of inositol-1,4,5-triphosphate ($InsP_3$) from phosphatidylinositol-4,5-biphosphate ($PIP_2$), in turn binding to $InsP_3$ receptors ($InsP_3R$) in order to trigger $Ca^{2+}$ release from intracellular endoplasmic reticulum (ER) stores (Gallo et al., Nat. Immunol. 7:25-32, 2006; Lewis et al., Annu. Rev. Immunol. 19:497-521, 2001), which results in an increase in cytosolic calcium levels that is dependent on the presence of coronin 1 (Jayachandran et al., Cell 130:37-50, 2007). Increase in cytosolic calcium results in the activation of calcineurin, which induces translocation of NFAT (nuclear factor of activated T cells) into the nucleus, where it activates genes essential for T cell activation and T cell immune responses (see FIG. 1). Inhibition of the calcineurin pathway results in reduced T cell mediated immune responses. Inhibitors of this pathway are commonly used to treat patients with autoimmune disorders as well as in prevention of immune responses following an organ transplantation that often results in the rejection of transplanted organ. The most widely used are the calcineurin inhibitors cyclosporin A (CsA) and FK506, which form complexes that ultimately inhibit calcineurin function. WO 2007/110385 describes the use of coronin 1 and coronin 1 modulators for the treatment of autoimmune and lymphoproliferative disorders and mycobacterial infections.

SUMMARY OF THE INVENTION

The invention relates to an assay for the identification of a compound having immunosuppressant activity, wherein a candidate compound is analyzed whether it blocks the $Ca^{2+}$ flux in coronin 1 expressing cells but not in coronin 1 negative cells. If a candidate compound is identified as blocking the $Ca^{2+}$ flux specifically in coronin 1 expressing cells, it likewise blocks T cell activation and T cell dependent immune responses and displays immunosuppressant activity.

In particular, the invention relates to an assay for the identification of a compound having immunosuppressant activity, wherein a coronin 1 expressing cell and a related cell negative for coronin 1, each comprising a calcium fluorophore, are incubated in the presence of a candidate compound, stimulated using anti-T cell receptor antibodies, or a phospholipase C activator such as m3M3FBS, or thapsigargin, and the fluorescence analyzed. Candidate compounds suppressing the $Ca^{2+}$ flux in coronin 1 expressing cells, but not in a related cell negative for coronin 1 are identified as having immunosuppressant activity.

A coronin 1 expressing cell is, for example, a wild type T cell, B cell, macrophage or mast cell. A related cell negative for coronin 1 is a corresponding T cell, B cell, macrophage and mast cell, respectively, wherein coronin 1 is knocked out or knocked down, e.g. by expressing coronin 1 specific siRNA, or a corresponding T cell, B cell, macrophage and mast cell, respectively, isolated from coronin 1 deficient knock-out laboratory animals, such as knock-out mice.

Another coronin 1 expressing cell is, for example, a non-leukocyte cell genetically engineered to express coronin 1. A related cell negative for coronin 1 is the corresponding non-transfected non-leukocyte cell.

The invention likewise relates to an upstream assay for the identification of a compound having immunosuppressant activity wherein a coronin 1 monomer or a peptide with a sequence spanning the trimerization site of coronin 1 in the coiled coil segment is tagged with either FRET acceptor or donor fluorescent tags or with yellow fluorescent protein fragments, the tagged peptides delivered inside non-leukocyte cells, which do not express coronin 1, or leukocyte cells wherein coronin 1 is knocked out or knocked down, incubated in the presence of candidate compounds, and the fluorescence analyzed. A candidate compound suppressing coronin 1 trimerization is identified as having immunosuppressant activity.

The invention likewise relates to a downstream assay for the identification of a compound having immunosuppressant activity, wherein DAG generation, $PIP_2$ levels and/or $InsP_3$ generation in coronin 1 expressing versus coronin 1 negative cells is measured. A candidate compound is identified as having immunosuppressant activity if DAG, $PIP_2$ and/or $InsP_3$ levels in coronin 1 expressing cells levels in presence of the candidate compound are comparable to DAG, $PIP_2$ and/or $InsP_3$ levels in comparable cells not expressing coronin 1.

The invention likewise relates to a downstream assay for the identification of a compound having immunosuppressant activity, wherein upon TCR triggering and in the presence of a candidate compound, cells are methanol or paraformaldehyde (PFA) fixed and stained for nuclei using a nuclear marker, as well as stained for NFAT, and the ratio of nuclear localization of NFAT versus the cytosolic localization of NFAT measured using immunofluorescence or laser scanning confocal microscopy. A candidate compound is identified as having immunosuppressant activity if the nuclear localization of NFAT is prevented in coronin 1 expressing cells.

Figure 1:
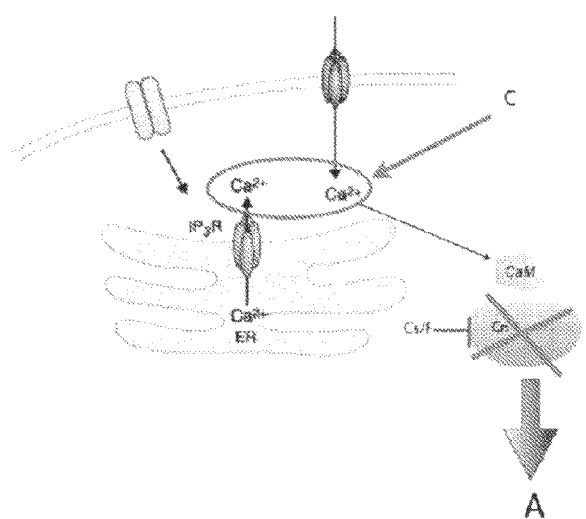
FIG. 1 Schematic representation of the role for coronin 1 in the activation of $Ca^{2+}$ mobilization and calcineurin activation; comparison with cyclosporin A or FK506. C=coronin 1; Cn=calcineurin; Cs=cyclosporin A; F=FK506; A=activation of T cells, CaM=calmodulin; $IP_3R$=inositol-1,4,5-triphosphate receptor; ER=endoplasmic reticulum.
Figure 2:
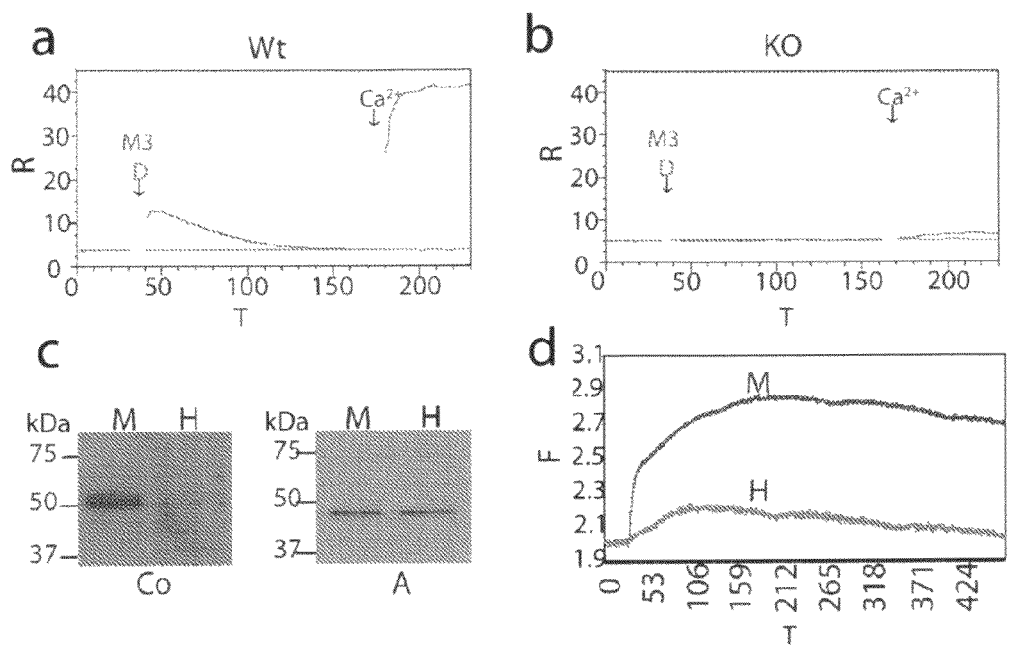
FIG. 2 (*a, b*) Total splenocytes from wild type (Wt, a) or coronin 1 deficient (KO, b) mice labeled with APC-conjugated anti-CD5 and PE-Cy7-conjugated anti-CD19 are loaded with Fluo-3 AM and stimulated with m3M3FBS (M3, upper line) or DMSO (D, lower line). Only PE-Cy7-negative CD5+ cells are included for the analysis. (*c*) Jurkat T cells transfected with pSUPER::hTACO1 (H=human siRNA) or pSUPER::mTACO1 (M=mouse siRNA). Immunoblot of total cell lysates of cells with coronin 1- (Co) or actin- (Ac)

specific antibodies. (d) Measurement of calcium flux by fluorescence in Jurkat T cells transfected as in (c) and then loaded with Indo-1 AM, stimulated with 10 μM m3M3FBS. (M=mouse siRNA; H=human siRNA).

Data are representative of three independent experiments. F=relative calcium flux; T=time in sec; kDa=molecular mass in kilodaltons.

DETAILED DESCRIPTION OF THE INVENTION

The invention relates to an assay for screening for compounds having immunosuppressant activity.

Since calcium levels play an important role in the activation of calcineurin and T cell mediated immune responses, searching for compounds that target the coronin 1 dependent signalling pathway can be based on read-out of calcium ($Ca^{2+}$) responses upon extracellular/intracellular stimuli. Hence molecules that block coronin 1 dependent $Ca^{2+}$ responses are candidates for the development of immunosuppressive compounds.

Unlike the $Ca^{2+}$/calcineurin pathway that is ubiquitously present and has various other functions (resulting in the observed side effects when using the known immunosuppressant compounds CsA or FK506), coronin 1 is expressed only in leukocytes, and therefore an inhibitor for coronin 1 dependent calcium fluxes is more specific to cells of the immune system, and the side effects of such a specific inhibitor are minimal.

Coronin 1 plays an important role in the activation of the $Ca^{2+}$/calcineurin pathway. Since coronin 1 is exclusively expressed in leukocytes such as T cells, B cells, macrophages, dendritic cells, mast cells, neutrophils, eosinophils, basophils, and NK killer cells, such cells can be used to analyze $Ca^{2+}$ responses, calcineurin activation, and/or leukocyte activation in a leukocyte specific manner.

The assay according to the invention is based on cells of lymphoid and myeloid lineage, both primary cells and cell lines, for example Jurkat, RBL, macrophage cell lines, bone marrow derived macrophages, and bone marrow derived mast cells, using $Ca^{2+}$ fluorimetry. Particular methods to be used comprise the known $Ca^{2+}$ fluorimetry systems with a fluorimeter, a FACSCAN fluorimeter, or single cell imaging. The assay is used to measure whether candidate compounds modulate the calcium responses as well as calcium levels inside a cell that is dependent on coronin 1. Useful candidate compounds block $Ca^{2+}$ fluxes in cells of lymphoid and myeloid lineage dependent on coronin 1, but neither in non-leukocytes nor in leukocytes lacking coronin 1 expression due to siRNA mediated knock down or due to other gene knockout technology, e.g. isolated from coronin 1 deficient laboratory animals, such us knockout mice.

Alternatively, this assay can also be based on non-leukocyte cells or cell lines, such as MelJuSo cells, fibroblasts, human embryonic kidney cells, and Chinese hamster ovary cell lines, in which leukocyte specific molecules comprising coronin 1, optionally in combination with other leukocyte specific molecules such as phospholipase C (PLC), are expressed through transfection. The assay selects those candidate compounds that inhibit $Ca^{2+}$ fluxes exclusively in the transfected cell lines and not in the parental cell line.

An assay according to the invention allows the determination whether a candidate compound targets the calcineurin activation pathway exclusively in leukocytes and not in other cell types. Selected candidate compounds are highly specific for leukocytes and lack the toxicity caused by blocking $Ca^{2+}$ fluxes in non-leukocytes.

Endoplasmic Reticulum Calcium Release

Triggering leukocytes with, e.g., anti-T cell receptor (TCR) antibodies, anti-IgM, or ATP, results in the release of calcium from the endoplasmic reticulum (ER) in a coronin 1 dependent manner. Once the ER calcium stores are depleted, this results in further increase in cytosolic calcium levels by a partially characterized mechanism that senses low ER calcium levels and secondarily activates calcium channels on the plasma membrane (M. Prakriya et al., Nature 443:230-3, 2006), thereby permitting calcium ions to flux from extracellular space and thus further amplifying cytosolic calcium levels. This secondary calcium flux across the plasma membrane in response to ER calcium store depletion is called plasma membrane calcium flux. The observations confirm that leukocytes harbour a signal transduction cascade that does not operate in non-leukocytes and is dependent on coronin 1. In the present invention it is found that the presence of a coronin 1 dependent signalling pathway can be used in a leukocyte-specific assay to screen for blockers of signal transduction pathways exclusively operating in leukocytes.

Studying the ER Calcium Release

Cells to be used are wild type T cells, B cells, macrophages, or mast cells, and corresponding T cells, B cells, macrophages, or mast cells, respectively expressing coronin 1 specific siRNA and hence having no coronin 1 expression, splenocytes from wild type mice and corresponding splenocytes from coronin 1 deficient knock-out mice, and, alternatively, a non leukocyte that does not express coronin 1 and the same cell line transfected with a coronin 1 expression vector. These cells are loaded with a calcium fluorophore, for example Indo 1-AM or Rhod 2-AM, or any other calcium sensitive fluorophore, for example Fluo-3, Fluo-4, Fura-2-AM (fluorophores from Invitrogen Technologies) for 10 min to 3 h at temperatures around 37° C. Particular preferred reaction conditions are around 45 min at around 37° C. and 5% $CO_2$ in the presence of 1 to 5 mM, in particular 2.5 mM, probenecid, and washing the cells thereafter, for example with calcium free HBSS/Ringer's solution (155 mM NaCl, 4.5 mM KCl, 10 mM D-glucose, 5 mM HEPES at pH 7.4, 1 mM $MgCl_2$ and 0.5 mM EGTA). Analysis is carried out using a fluorimeter or flow cytometric system or single cell imaging system in the presence of candidate compounds undergoing screening. Cells can be stimulated with either anti-TCR antibodies, a phospholipase C (PLC) activator such as m3M3FBS (2,4,6-trimethyl-N-(meta-3-trifluoromethyl-phenyl)-benzenesulfonamide), or thapsigargin, an inhibitor of calcium pump in endoplasmic reticulum named SERCA (for Sarco/Endoplasmic Reticulum Calcium ATPases) as a control. Normally, this pump aids in pumping calcium ions from the cytosol into the endoplasmic reticulum. Inhibiting its function results in increase in cytosolic calcium levels and enhanced fluorescence by the calcium sensitive fluorophores.

Studying the Plasma Membrane Calcium Flux

The cells mentioned in the preceding paragraph are loaded with any of the chemical calcium sensitive fluorophore as described or transfected to express aequorin. Analysis is carried out using a fluorimeter or flow cytometric system or single cell imaging system in the presence of candidate compounds and stimulated with either anti-TCR antibodies, a PLC activator such as m3M3FBS, or thapsigargin followed by the addition of calcium chloride.

In a particular experimental set-up, cells are loaded with calcium sensitive fluorophores and perfused initially with 0.5 mM $Ca^{2+}$ Ringer's solution and then stimulated with either anti-TCR antibodies, or a PLC activator such as m3M3FBS, or thapsigargin in the presence or absence of the candidate compound undergoing screening in $Ca^{2+}$ free Ringer's solution (1 mM ethyleneglycol tetraacetate (EGTA), 4.5 mM KCl) to stimulate ER calcium depletion. This is followed by perfusion of a high potassium Ringer's solution (149.5 mM KCl, 10 mM NaCl) with 1 mM $Ca^{2+}$ to assess CRAG dependent $Ca^{2+}$ entry. Finally $Ca^{2+}$-free Ringer's solution (1 mM EGTA, 4.5 mM KCl) is perfused to assess $Ca^{2+}$ extrusion rates.

Aequorin Based ER and Plasma Membrane Calcium Flux Analysis

Alternatively, instead of using any of the chemical calcium fluorophores mentioned above, the calcium flux analysis is carried out using the biological calcium fluorophore aequorin. Wild type coronin 1 positive cells and corresponding knock-out or knock-down coronin 1 negative cells are transfected with an expression construct for aequorin, 3-5 days post transfection the cells are stimulated with either anti-TCR antibodies, a PLC activator such as m3M3FBS, or thapsigargin, and changes in the fluorescence intensity of aequorin measured. The same assay is carried out in the presence of candidate compounds, and a candidate compound is identified as having immunosuppressant activity if it reduces the calcium flux in the analyzed cells.

PLC activation: In this assay calcium fluxes are measured in leukocytes upon stimulation with a PLC activator such as m3M3FBS in the presence of candidate compounds. A desired candidate compound blocks the ER calcium flux as well as plasma membrane dependent calcium flux in wild type cells. Alternatively, siRNA dependent knock down of coronin 1 expression in leukocytes brings down the ER as well as plasma membrane calcium fluxes.

In a particular experimental set-up for analysis of PLC activation, cells are loaded with any of the calcium sensitive fluorophores mentioned above, washed and re-suspended in HBSS or a similar medium, without calcium and in the presence of EGTA, e.g. 0.5 mM EGTA. The cells are treated with either a PLC activator such as m3M3FBS (10 to 50 μM) or DMSO or another control to assess the ER calcium release followed by the addition of $Ca^{2+}$, e.g. 1 to 2 mM $CaCl_2$, to assess the plasma membrane calcium fluxes. The changes in the fluorescence are measured using a fluorimeter or flow cytometry or single cell imaging (FIG. 2).

For the analysis of $Ca^{2+}$ mobilization in other leukocytes expressing coronin 1 and associated genes in the pathway, such as phospholipase C (PLC), they are transfected with 2 μg each of pSUPER::mTACO1 for suppressing murine coronin 1 expression or pSUPER::hTACO1 for suppressing human coronin 1 expression. For non-leukocytes, these are transfected with expression constructs containing the coronin 1 cDNA (see J. Gatfield et al., Mol Biol Cell 16:2786-98, 2005) and associated genes in the pathway, such as phospholipase C (PLC).

The following oligonucleotides are employed as siRNA directed against mouse coronin 1 (siRNAmCORO1nt198-216, target sequence in italics):

(forward oligonucleotide, SEQ ID NO: 1)
5'-GATCCCC*GACTGGACGAGTAGACAAG*TTCAAGAGA*CTTGTCTACTC GTCCAGTC*TTTTTGGAAA-3'
and (reverse oligonucleotide, SEQ ID NO: 2)
5'-AGCTTTTCCAAAAA*GACTGGACGAGTAGACAAG*TCTCTTGAA*CTTG TCTACTCGTCCAGTC*GGG-3'.

The following oligonucleotides are used as siRNA directed against human coronin 1 (siRNAhCORO1 nt594-612, target sequence in italics):

(forward oligonucleotide, SEQ ID NO: 3)
5'-GATCCCCGC*GCGTGCGCATCATCGAG*TTCAAGAGA*CTCGATGATGC GCACGCGC*TTTTTGGAAA-3'
and (reverse oligonucleotide, SEQ ID NO: 4)
5'-AGCTTTTCCAAAAA*GCGCGTGCGCATCATCGAG*TCTCTTGAA*CTCG ATGATGCGCACGCGC*GGG-3'.

If human cells lines are used, oligonucleotides of SEQ ID NO:1 and 2 serve as controls, and if murine cells are used, oligonucleotides of SEQ ID NO:3 and 4 serve as controls.

After 1 to 7 days post transfection cells are loaded with any of the calcium sensitive fluorophore, such as Indo 1-AM or Rhod2-AM, washed, and re-suspended in HBSS with 2 mM $Ca^{2+}$ or another calcium-containing medium. The cells are treated with either anti-TCR antibodies, a PLC activator such as m3M3FBS, or DMSO or another control such as thapsigargin to assess the changes in the calcium fluxes using any of the above mentioned fluorimetric techniques. In such an assay, coronin knockdown results in reduced calcium fluxes.

Upstream Assays

These are assays that are directly or indirectly upstream of coronin 1 dependent calcium flux generation. It had been shown (J. Gatfield et al., Molecular Biology of the Cell 16:2786-2798, 2005) that coronin 1 is a homotrimer, and that trimerization is needed for its cytoskeletal association and hence for its normal activity. Coronin 1 is organized into three domains: 1) an N-terminal, WD repeat-containing β-propeller connected by 2) a linker region to 3) a coiled coil (cc). Cytoskeletal association occurs exclusively upon trimerization that is mediated via the coiled coil domain. Hence, any chemical or biological moiety, in particular a candidate compound, that negatively affects the trimerization state of coronin 1 is likely to result in suppression of coronin 1 dependent calcium fluxes and thereby cause immunosuppression. Further confirmation is obtained by using peptide sequences (R. A. Kammerer, Proceedings of the National Academy of Sciences 102:13891-13896, 2005) spanning the putative trimerization site of coronin 1 shown to be present in the coiled coil (cc) segment. The ccCor1 peptides (the wild type sequence corresponds to residues Val430-Lys461 of mouse coronin 1) show that the distinct electrostatic interaction network formed between the guanidinium group of Arg450 and the Asp452 and Glu455 side chains controls the three-stranded coiled-coil formation of ccCor1.

The trimerization assay is based on principles involving fluorescence energy transfer (FRET). FRET is the transfer of energy from a donor dye to an acceptor dye during which the donor emits the smallest possible amount of measurable fluorescent energy. In this method a fluorescent dye donor is, for example, excited with light of a suitable wavelength. Due to its spatial vicinity to a suitable second dye, the acceptor, this results in a radiation-free energy transfer to the acceptor. If the second dye is a fluorophore or luminophore, the light emitted by this second dye at a particular wavelength can be used for a qualitative as well as for a quantitative determination.

For the coronin trimerization assay based on FRET, either the full length coronin 1 monomers or a ccCor1 peptide, for example a peptide of SEQ ID NO:5

VSRLEEDVRNLNAIVQKLQERLDRLEETVQAK, (SEQ ID NO: 5)

are tagged with either acceptor or donor fluorescent tags and allowed to trimerize under optimal conditions in the presence of candidate compounds and screened for inhibition of homotrimerization. A candidate compound having the capacity to prevent trimerization of coronin 1 monomers is useful as a immunosuppressant.

In a cell based assay system based on FRET or YFP (yellow fluorescent protein) fragment complementation, the tagged full length coronin 1 monomers or a ccCor1 peptide are delivered inside non-leukocytes, which do not express coronin 1, or leukocytes wherein coronin 1 is knocked down or knocked out, using e.g. liposomes, coronin 1 is allowed to trimerize inside the cells in the presence of a candidate compound, and analyzed for inhibition of homotrimerization. The candidate compound with the desired property has the capacity to prevent trimerization of coronin 1 monomers as judged by FRET.

Alternatively, full length coronin 1 or the trimerization motif alone is cloned in two different vectors such as, for example, pCDMA-YFP (Clonetech) carrying two different YFP constructs. Both vectors are simultaneously transfected into non-leukocytes, which do not express coronin 1, or leukocytes wherein coronin 1 is knocked down or knocked out, and allowed to trimerize inside the cells. Some trimers will have at least one monomeric subunit belonging to both the YFP constructs. This results in complementation to generate the full YFP molecule, which will fluoresce and can be detected. Fluorescence is monitored in the presence of candidate compounds and analyzed for inhibition of trimerization.

Downstream Assays

In T cells coronin 1 interacts with phospholipase C (PLC) and is essential for the generation of inositol-1,4,5-triphosphate ($InsP_3$) upon T cell receptor stimulation from phosphatidyl-inositol-4,5-biphosphate ($PIP_2$), thereby mediating $Ca^{2+}$ release from intracellular stores that is essential for T cell activation and survival. While in the absence of coronin 1, the $Ca^{2+}$-dependent translocation of nuclear factor of activated T cells (NFAT) to the nucleus is defective upon T cell receptor (TCR) stimulation in coronin 1-deficient T cells, TCR triggering induces similar nuclear translocation of NE-KB. These results are consistent with a specific role for coronin 1 in $InsP_3$ mediated $Ca^{2+}$ release and furthermore shows that deletion of Coro1a does not result in a general defect in TCR-mediated signalling. The process of $InsP_3$ generation from $PIP_2$ by PLC also results in the generation of diacyl glycerol (DAG). Further downstream assays therefore include the analysis of diacyl glycerol (DAG) content, $PIP_2$ levels as well as $InsP_3$ levels.

DAG, $PIP_2$ and $InsP_3$ Generation

Activation of PLC leads to the generation of inositol-1,4,5-triphosphate ($InsP_3$) and diacyl glycerol (DAG) from phosphatidylinositol-4,5-biphosphate ($PIP_2$). $InsP_3$ binds to $InsP_3$ receptors ($InsP_3R$) and triggers $Ca^{2+}$ release from intracellular stores (E. M. Gallo et al., Nat Immunol 7:25, 2006). Triggering of the T cell receptors of coronin 1-deficient T cells results in a drastically reduced $InsP_3$ generation from $PIP_2$ compared to wild-type T cells. Moreover it is shown by immunohistochemistry that in wild type cells, all of the $PIP_2$ disappears within 45 sec following TCR stimulation. Consistent with defective $InsP_3$ generation in the absence of coronin 1, $PIP_2$ levels remain unaltered when the T cell receptors of coronin 1-deficient T cells are stimulated. Therefore, alternative assays are based on the analysis of DAG generation, $PIP_2$ levels and $InsP_3$ generation in coronin 1 expressing versus coronin 1 negative cells. A candidate compound is identified as having immunosuppressant activity if DAG, $PIP_2$ and/or $InsP_3$ levels in coronin 1 expressing cells in presence of the candidate compound are comparable to DAG, $PIP_2$ and/or $InsP_3$ levels in comparable cells not expressing coronin 1.

DAG assay: DAG content is determined, for example, by the conversion to phosphorylation products by externally added DAG-kinase from *E. coli* in the presence of [$\gamma$-$^{32}$P] ATP (J. Preiss et al., J. Biol. Chem. 261:8597-8600, 1986).

$PIP_2$ assay: Levels of $PIP_2$ can be measured using flow cytometry and anti-$PIP_2$ antibodies, for example using cells fixed with paraformaldehyde (3%) after stimulation with anti-TCR antibodies or a PLC activator. Alternatively, $PIP_2$ levels can be determined by immunofluorescence microscopy on cells stimulated with either anti-TCR antibodies or a PLC activator and followed by fixation in paraformaldehyde.

$InsP_3$ assay: Splenic naïve T-cells are isolated and starved, for example for 2 h in medium without FBS at 37° C., 5% $CO_2$, then coated with anti-CD3 (e.g. 10 μg/ml) or anti-CD3 plus anti-CD28 (e.g. 10 μg/ml each) for 10 to 60 min, e.g. 15 min, on ice, washed once in serum free medium to remove unbound antibody, and TCRs are cross-linked with a secondary antibody (e.g. mouse anti-hamster) for 0, 45, 90 and 120 seconds at 37° C. in a water bath. Alternatively, cells can be stimulated with a PLC activator such as m3M3FBS. $InsP_3$ levels can be analyzed using a competitive radio-receptor assay kit according to the manufacturers protocol (Perkin Elmer).

The above mentioned differences between wild type and coronin 1 deficient leukocytes can be exploited in the identification of candidate compounds that are interfering with the coronin 1 dependent downstream $InsP_3$/DAG generation. Such a candidate compound specifically blocks the coronin dependent $InsP_3$/DAG signalling in normal wild type cells, which can be confirmed by the absence of any of its interference in $InsP_3$/DAG signalling in coronin 1 knock out or knock down leukocytes by other coronin 1 independent pathways.

NFAT Translocation

In the absence of coronin 1, $Ca^{2+}$-dependent translocation of nuclear factor of activated T cells (NFAT) to the nucleus is defective upon TCR stimulation or by a PLC activator such as m3M3FBS in coronin 1-deficient T cells but not in wild type T cells. Measuring translocation of NFAT further allows the identification of suitable candidate compounds.

Upon TCR triggering and in the presence of a candidate compound, cells are methanol or PFA fixed and stained for nuclei using nuclear marker, for example DAPI or propidium iodide, along with antibodies to NFAT, and the ratio of nuclear localization of NFAT versus the cytosolic localization of NFAT is monitored using immunofluorescence microscopy. This procedure is automated using 96 well format and high throughput immunofluorescence or laser scanning confocal microscopy. Useful candidate compounds inhibit the nuclear localization of NFAT upon TCR stimulation in wild type cells but not in coronin 1 deficient cells, showing its dependence on coronin 1 pathway.

EXAMPLES

Mice

Mice lacking coronin 1 are generated as described (R. Jayachandran et al., Cell 130:37-50, 2007). Experiments shown are performed with mice that were backcrossed to C57BL/6 for at least four generations, using wild-type littermates as a control.

Biochemical Methods

Cell homogenization, lysis and immunoblotting is performed as described (A. Tulp et al., Nature 369:120-126, 1994; G. Ferrari et al., Cell 97:435-47, 1999; J. Pieters et al., J Cell Biol 115:1213-23, 1991). Polyclonal anti-coronin 1 serum has been described before (J. Gatfield et al., Mol Biol Cell 16:2786-98, 2005). Anti-$PIP_2$ antibodies (clone 2C11)

are from Santa Cruz. Antibodies against PLC-γ1 and P-PLC-γ1 are from Cell Signaling Technology. Anti-CD3 and anti-CD28 are from BD Biosciences and the secondary mouse anti-hamster is from R&D. Anti-NFAT antibody is from Santa Cruz.

Immunofluorescence Microscopy

Cells are adhered on poly-L-lysine coated 10 well Teflon-coated glass slides (Polysciences) for 20 min on ice. Cells are fixed with methanol or 4% paraformaldehyde (PFA) and then blocked and permeabilized in PBS, 3% BSA, 0.1% TritonX-100. The cells are then stained for 60 min at room temperature (RT) with appropriate primary antibodies (anti-NFAT, anti-PLC gamma, anti-coronin 1, anti-$PIP_2$) and the corresponding secondary antibodies (goat anti-mouse Alexa Fluor 546, goat anti-rabbit Alexa Fluor 488) are applied for 45 min at RT (1:200 for second antibodies). Slides are washed extensively and mounted using FLUOROGUARD antifade mounting medium (BioRad). Slides are analyzed using conventional immunofluorescence or laser scanning confocal microscopy using for example the LSM510 Meta (Zeiss) and the corresponding software. All the experiments are carried out in the absence and presence of the candidate compound.

TCR Signalling and $InsP_3$ Measurements

Isolated naïve splenic T-cells are starved for 2 h in medium without FBS at 37° C., 5% $CO_2$, coated with anti-CD3 (10 μg/ml) or anti-CD3 plus anti-CD28 (10 μg/ml each) for 15 min on ice, washed once in serum free medium to remove unbound antibody, and TCRs are cross-linked with a secondary antibody (mouse anti-hamster) for the indicated times at 37° C. in a water bath. $InsP_3$ levels are analyzed using a competitive radio-receptor assay kit according to the manufacturers protocol (Perkin Elmer). All the experiments are carried out in the absence and presence of the screening candidate compound.

$Ca^{2+}$ Mobilization Measurements

Total spleen cell suspensions are subjected to erythrocyte lysis, washed with RPMI 1640 (Gibco) supplemented with 3% heat inactivated FCS (Gibco) and loaded with Indo-1 by incubation in 3 μg/ml of Indo-1 AM or 3 μg/ml of Fluo-3 AM (Molecular Probes) for 45 min at 37° C. in the dark. After loading, cells are washed one to two times with RPMI 1640 containing 3% FCS, and stained with anti-CD19-PE (Indo-1), anti-CD19-APC (Fluo-3) (clone 1D3, BD Pharmingen) and anti-CD11b-PE (Indo-1), anti-CD11b-APC (Fluo-3) (clone M1/70, BD Pharmingen) for 30 min on ice. Cells are subsequently washed twice with RPMI 1640/3% FCS or calcium free Ringer solution. After equilibration of the cells at 37° C. for 5-10 min and establishing a base line for 30 sec, calcium flux is induced by TCR crosslinking using anti-CD3 (7.5-10 μg/ml; clone 145-2C11, BD Pharmingen), anti-CD28 (5 μg/ml) and mouse anti-hamster IgG (5 μg/ml, clone MAH1.12, RD Systems) (E. Teixeiro et al., Immunity 21:515-26, 2004). Cells are analyzed by flow cytometry on a FACSVantage, FACSCalibur or a LSR II for an additional 9-9.5 min measuring the FL4/FL5 ratio (Indo-1) or the FL2-H signal (Fluo-3). Only PE or APC negative cells are considered for calcium mobilization measurements. Thymocytes are loaded with Indo-1 as described above, labeled with PE and PE-Cy7 conjugated anti-CD4 and anti-CD8 for 30 min on ice and triggered with 5-7.5 μg/ml, clone 145-2C11, BD Pharmingen and mouse anti-hamster IgG (5 μg/ml, clone MAH1.12, RD Systems). For analysis of PLC activation, cells are loaded with Fluo3 AM (2 μM) and labeled with APC conjugated anti-CD5 antibody (to detect T cells) and PE-Cy7 conjugated anti-CD19 antibody (to exclude B cells). Cells are washed and re-suspended in HBSS without calcium in the presence of 1 mM EGTA. The cells are treated with either a PLC activator (m3M3FBS, 10 μM) or DMSO at the indicated time points followed by the addition of 2 mM $CaCl_2$. For analysis, only PE-Cy7 negative CD5 positive cells are included. Data are analyzed using FlowJo software. All the experiments are carried out in the absence and presence of the candidate compound.

For the analysis of $Ca^{2+}$ mobilization in Jurkat T cells, Jurkat cells are transfected with 2 μg each of pSUPER::mTACO1 or pSUPER::hTACO1 as described. Transfected or un-transfected cells are loaded with Indo 1-AM (4 μg/ml) for 45 min in RPMI with 10% FBS at 37° C. Cells are washed in HBSS without calcium (Invitrogen/GibcoBRL) and seeded at 50,000 cells per well in a 96 well special optics black plates (Costar corning). Cells are stimulated with 10 μM m3M3FBS after 30 seconds and the changes in fluorescence emission at 405 nm and 480 nm measured with excitation at 340 nm using Synergy 2 multi-detection microplate reader for a period of 8 minutes. The ratio of 405/480 emission values is calculated and normalized using the software provided. All the experiments are carried out in the absence and presence of the candidate compound.

Aequorin Based Calcium Analysis $5×10^5$ cells from both the coronin 1 expressing as well as the control coronin 1 negative cells are seeded in culture dishes and allowed to attain 80% confluency in appropriate culture media containing 10% FBS and 5% $CO_2$ at 37° C. The cells are transfected with 2 μg of pCMV IRES Aequorin vector and allowed to grow for additional 3 days, at the end of which they are stimulated with either anti-TCR antibodies (10 μg/ml of hamster anti-CD3 and anti-CD28) followed by mouse anti-hamster antibody, a PLC activator or 1 μM thapsigargin, and changes in the fluorescence intensity of aequorin measured using a fluorimeter or flow cytometry. For screening of the candidate compounds that reduce the calcium fluxes, the cells are preincubated for 2 hours with the candidate compound under screening with appropriate buffer controls and taken for stimulation and analyses.

Cell Based FRET Assay

Coronin 1 negative cells (as mentioned above) are cultured in their appropriate culture medium with 10% fetal bovine serum (FBS) at 37° C. and 5% $CO_2$ in clear optics chambered cover glasses. When 80% confluency is attained, the culture medium is replaced with serum free OPTIMEM medium (Invitrogen technologies) along with liposomes loaded with FRET acceptor and FRET donor tagged ccCoronin 1 peptide sequences in equimolar ratio (corresponding to the coiled domain of coronin 1, SEQ ID NO:5) and allowed to get internalized for 30 min. Alternatively, peptides are introduced into the cells by electroporation. The cells are washed to remove the uninternalized peptides and the fluorescence of the FRET pairs analyzed using fluorescence microscopy. In parallel, cells from few of the cover glasses treated similarly are scraped and resuspended and taken for flow cytometry and spectrometry based analyses for the fluorescence intensity. All the experiments are carried out in the absence and presence of the candidate compound.

Nuclear Translocation of NFAT $1×10^6$ wild type or any other coronin 1 expressing spleenic T cell as well as coronin 1-deficient or appropriate coronin 1 negative splenic T cell previously incubated with various candidate compounds or appropriate controls at 37° C. and 5% $CO_2$ for 2 hours are coated with anti-CD3 (10 μg/ml) and anti-CD28 (5 μg/ml) on ice or left untreated as an antibody control. After washing, T cell receptors are cross-linked by adding mouse anti-hamster antibodies to a final concentration of 10 μg/ml. Cells are incubated at 37° C. in a water bath for 20 or 30 minutes and reactions stopped by adding ice cold PBS/2% FBS/0.05% sodium azide. After washing, cells are incubated with Alexa Fluor-488 goat anti-mouse on ice for 15 minutes to stain the TCR caps. Washed cells are fixed in 8% PFA for 20 minutes at room temperature and stained with anti-NFAT antibody (Santa Cruz). Nuclei are stained using DRAQ5. For quantization of nuclear translocation of NFAT cells are analyzed for both wild-type as well as coronin 1-deficient T cells.

The invention claimed is:

1. An assay for identifying a compound suppressing coronin 1 trimerization, comprising:
    tagging peptides that are either (i) coronin 1 monomers or (ii) peptides comprising a peptide of SEQ ID NO: 5, with either fluorescence resonance energy transfer (FRET) acceptor or donor fluorescent tags resulting in tagged peptides carrying an acceptor tag and tagged peptides carrying a donor tag, or
    with yellow fluorescent protein (YFP) fragments resulting in tagged peptides carrying one type of YFP fragment and tagged peptides carrying a fragment complementary to said one type of YFP fragment, wherein the tagged peptides are:
    delivered inside non-leukocyte cells that do not express coronin 1, or leukocyte cells in which coronin 1 is knocked out or knocked down, and
    incubated in the presence of one candidate compound,
    wherein fluorescence is analyzed, and if the candidate compound suppresses fluorescence from FRET or YFP complementation, the candidate compound is identified as a compound suppressing coronin 1 trimerization.

2. The assay according to claim 1 wherein the fluorescence is analyzed with a fluorimeter, automated flow cytometer or single cell imaging.

3. The assay according to claim 1 wherein the tagged peptides are delivered inside leucocyte cells wherein coronin 1 is knocked down using siRNA.

4. The assay according to claim 1, wherein the tagged peptides are delivered inside leucocyte cells isolated from coronin 1 deficient knock out mice.

* * * * *